United States Patent [19]

Studt et al.

[11] 4,436,911

[45] Mar. 13, 1984

[54] HETEROCYCLIC AMIDINOUREAS

[75] Inventors: William L. Studt, Harleysville; Harry K. Zimmerman, Quakertown; George H. Douglas, Malvern, all of Pa.

[73] Assignee: William H. Rorer, Inc., Fort Washington, Pa.

[21] Appl. No.: 262,811

[22] Filed: May 12, 1981

[51] Int. Cl.³ .................... C07D 213/77; A61K 31/44
[52] U.S. Cl. .................................... 546/291; 546/292; 546/293; 546/294; 546/289; 546/305; 546/306; 424/263; 424/266
[58] Field of Search ............... 546/306, 305, 292, 293, 546/289, 294, 291

[56] References Cited

U.S. PATENT DOCUMENTS 4,220,658 9/1980 Douglas et al. .................... 424/304
4,225,315 9/1980 Won et al. ...................... 23/230 PC
4,279,928 7/1981 Riley et al. .......................... 424/324

OTHER PUBLICATIONS

Bickel, Pharmacological Reviews, vol. 21, (4), pp. 325-343, Williams & Wilkins Pub., (Dec. 1969).

*Primary Examiner*—Alan L. Rotman
*Attorney, Agent, or Firm*—James A. Nicholson; Alexis Barron; Martin F. Savitzky

[57] ABSTRACT

This invention relates to a novel class of heterocyclic amidinourea and heterocylic amidinothiourea compounds wherein the heterocyclic substitution is at the 1-N urea nitrogen atom. These compounds exhibit pharmaceutical activity and may be incorporated into pharmaceutical preparations for producing anti-ulcerogenic, antisecretory, antispasmodic, antimotility, cardiovascular, antidiarrheal or antiparasitic action.

12 Claims, No Drawings

HETEROCYCLIC AMIDINOUREAS

FIELD OF THE INVENTION

This invention relates to a novel class of heterocyclic amidinoureas and heterocyclic amidinothioureas that exhibit pharmacological activity and may be incorporated into a pharmacological preparation useful for producing cardiovascular, gastrointestinal and antiparasitic action.

REPORTED DEVELOPMENTS

The phenylamidinoureas have been reported as possessing antisecretory, antispasmodic, anti-ulcerogenic, anesthetic, antidiarrheal and antihypertensive activity in a series of recent patents and publications. See, Arzneimittel Forschung, (Drug Research) 28 (II), 1443–1480 (1978), and U.S. Pat. Nos. 4,025,652, 4,058,557, 4,060,635, 4,088,785, 4,115,564, 4,115,647, 4,117,165, 4,147,804, 4,150,154, 4,169,115, 4,178,387, 4,204,000, and 4,220,658.

This invention relates to a novel class of amidinoureas substituted by a heterocyclic group, possessing pharmaceutical activity including, for example, blood pressure lowering activity.

SUMMARY OF THE INVENTION

This invention relates to a novel class of compounds according to Formula I

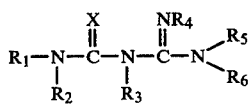

where:

X is O or S;

$R_1$ is a 5 to 7 atom ring or a 7 to 13 atom fused or bridged ring which may include 1 to 4 hetero atoms of N, O or S; and containing a total of about 3 to about 20 carbon atoms; and the N— or S— oxides thereof;

$R_2$, $R_3$ and $R_4$ are hydrogen or lower alkyl;

$R_5$ and $R_6$ are hydrogen, alkyl, cycloalkyl, aralkyl, alkenyl, aryl, alkoxy or a heterocyclic group, or $R_5$ and $R_6$ together with the nitrogen to which they are attached form a 3 to 7 atom ring which may include 0 to 2 additional hetero atoms of N, O or S;

and the nontoxic acid addition salts thereof.

Compounds according to Formula I exhibit pharmaceutical activity including, for example, blood pressure lowering activity. This invention also relates to a method for the treatment of human and veterinary gastrointestinal disorders, cardiovascular disorders, spasmolytic disorders and parasitic infestations by the administration of a compound according to Formula I.

Preferred compounds of this invention include amidinoureas substituted in the $R_1$ position by pyridyl, pyridyl N-oxide, thiophenyl, pyrrole, dihydroquinolinyl, quinolinyl, and dihydroindolinyl, among others.

DETAILED DESCRIPTION OF THE INVENTION $R_1$ in Formula I above may be any one of the following heterocyclic groups: 1-pyrrole, 2-pyrrole, 3-pyrrole, 2-furan, 3-furan, 2-thiophene, 3-thiophene, 2-tetrahydrothiophene, 3-tetrahydrothiophene, 1-imidizole, 2-imidizole, 4-imidizole, 5-imidizole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 1-(3-pyrroline), 2-(3-pyrroline), 3-(3-pyrroline), 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, or carbazole.

The heterocyclic groups may be mono-, di-, tri- or tetra-substituted by ring substituents such as lower alkyl, lower alkenyl, aryl, lower alkynyl, aralkyl, halo, nitro, cyano, sulfonyl, hydroxyl, carboxyl, lower alkanoyl, lower alkoxy, aryl lower alkoxy, halo lower alkoxy, amido, amino, lower alkyl amino, acyloxy, carbamoyl, lower alkoxyamino, and aralkoxyamino.

Preferred compounds of this invention are those where:

$R_1$ is a substituted or unsubstituted 5 or 6 membered hetero ring containing 1 to 3 hetero atoms of sulfur, oxygen or nitrogen, and S- and N-oxides thereof:

$R_2$ is hydrogen or lower alkyl;

$R_3$ and $R_4$ are hydrogen; and $R_5$ and $R_6$ are hydrogen, lower alkyl, cyclo lower alkyl, lower alkoxy, alkenyl, aryl, aralkyl, or a heterocyclic group, or $R_5$ and $R_6$ together with the nitrogen to which they are attached form a 3 to 7 atom ring which may include 0 to 2 additional hetero atoms of N, O or S;

and non-toxic acid addition salts thereof.

One preferred embodiment of this invention is a compound described by any of Formulae II–IV

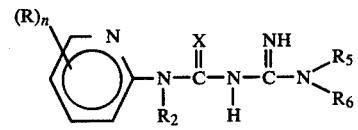

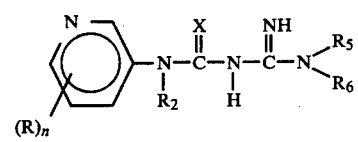

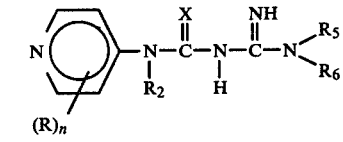

where:

n is 0 to 4;

X is O or S;

(R) represents a ring substituent selected from the group including lower alkyl, lower alkoxy, lower alkenyl, lower alkynyl, aralkyl, aryl, alkaryl, nitro, halo, cyano, lower alkanoyl, carboxyl, sulfonyl, amino, lower alkylamino, lower alkyl acyloxy, lower alkylamido, amino lower alkyl, carbamoyl, halo lower alkyl, hydroxy and the N-oxide of the pyridyl nitrogen atom;

$R_2$ is hydrogen or lower alkyl;

$R_5$ and $R_6$ are hydrogen, lower alkyl, cycloalkyl, aryl, lower alkenyl, aralkyl, lower alkoxy, or heterocycle;

$R_5$ and $R_6$ together form a 3 to 7 atom ring which may include 1 to 3 hetero atoms of N, O or S;
and the non-toxic acid addition salts thereof.

Another preferred embodiment of this invention is a compound according to Formula V or VI

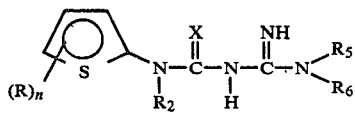   V

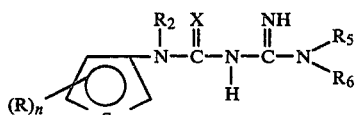   VI where:
X is O or S;
n is 0 to 3;
(R) represents a ring substituent selected from the group including lower alkyl, lower alkoxy, lower alkenyl, lower alkynyl, aralkyl, aryl, alkaryl, nitro, halo, cyano, carbamoyl, lower alkyl acyloxy, carboxyl, sulfonyl, amino, lower alkanoyl, lower alkylamino, amino lower alkyl, lower alkyl amido, halo lower alkyl, hydroxy and the S-oxides of the thiophene sulfur atom, such as, a thiophenyl sulfoxide or thiophenyl sulfone;
$R_2$ is hydrogen or lower alkyl;
$R_5$ and $R_6$ are hydrogen, lower alkyl, cycloalkyl, aryl, lower alkoxy, lower alkenyl, aralkyl, or heterocycle or $R_5$ and $R_6$ together with the nitrogen to which they are attached form a 3 to 7 membered ring which may include 0 to 2 additional hetero atoms of N, O or S;
and the non-toxic acid addition salts thereof.

In any discussion of the true structure of an amidinourea, tautomerism must be considered. It should be clear to anyone skilled in the art that the amidinourea side chain can be legitimately represented in any one of several tautomeric forms. In solution, one form may predominate over another, depending upon the degree and location of substitution and on the nature of the solvent. The rates of conversion of one tautomer to another will depend upon the nature of the solvent, the degree of hydrogen bonding permitted, the temperature, and possibly other factors (such as pH, trace impurities and the like).

To illustrate what is meant by this, a number of tautomeric structures are here shown for just one of the compounds of this invention:

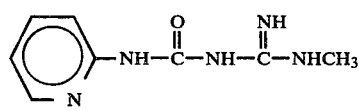

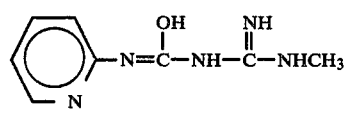

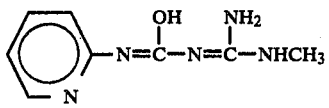

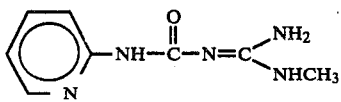

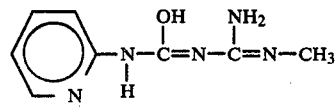

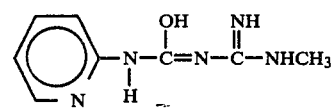

Of course, other structures are possible, such as those with hydrogen bonding.

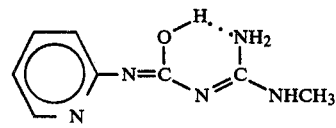

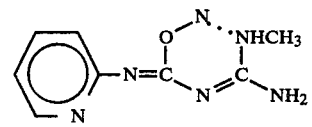

Furthermore, the heterocyclic atom may contribute to structures reflecting hydrogen bonding.

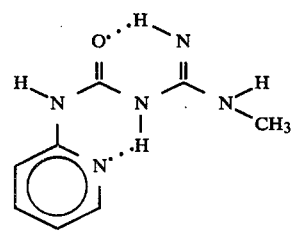

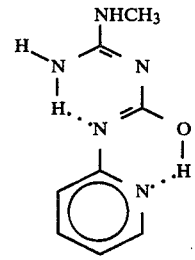

As employed above and throughout the disclosure, the following terms, unless otherwise indicated, shall be understood to have the following meanings.

"Alkyl" means a saturated aliphatic hydrocarbon which may be either straight- or branched-chain. Preferred alkyl groups have no more than about 12 carbon atoms and may be methyl, ethyl and structural isomers of propyl, butyl, pentyl, hexyl, heptyl, octyl, nonyl, decyl, undecyl and dodecyl. Also included are the cycloalkyl groups such as cyclopropyl, cyclopentyl, cyclohexyl, etc., and the cycloalkylalkyl groups such as cyclopropylmethyl and the like.

"Lower alkyl" means an alkyl group as above, having about 1 to 6 carbon atoms. Suitable lower alkyl groups are methyl, ethyl, n-propyl, isopropyl, butyl, sec-butyl, tert-butyl, n-pentyl, isopentyl and neopentyl.

"Cycloalkyl" means an aliphatic monocyclic saturated carbocyclic group. Preferred groups have 3 to 6 carbon atoms, for example, cyclopropyl, cyclopentyl and cyclohexyl.

"Alkenyl" means an unsaturated aliphatic hydrocarbon. Preferred alkenyl groups have no more than about 12 carbon atoms and 1 to 3 carbon-carbon double bonds and may include straight or branched chains, and may be any structural and geometric isomers of ethenyl, propyenyl, butenyl, pentenyl, hexenyl, heptenyl, octenyl, nonenyl, decenyl, undecenyl, and dodecenyl or butadienyl, pentadienyl etc. Also included are the cycloalkylene groups such as cyclopropenyl, cyclopentenyl, cyclohexenyl, etc. and the cycloalkylalkylene groups such as cyclopropylenylmethyl, cyclohexenylmethyl and the like.

"Lower alkenyl" means alkenyl of 2 to 6 carbon atoms such as ethylene, propylene, butylene, isobutylene, etc., including all structural and geometrical isomers thereof.

"Alkynyl" means an unsaturated aliphatic hydrocarbon. Preferred groups have no more than about 12 carbon atoms and contain one or more triple bonds, including any structural or geometric isomers of acetylenyl, propynyl, butynyl, pentynyl, hexynyl, heptynyl, octynyl, nonynyl, decynyl, undecynyl, dodecynyl, etc.

"Lower alkynyl" means alkynyl of 2 to 6 carbon atoms such as structural and geometric isomers of propargyl, butynyl, pentynyl, etc.

"Aryl" means phenyl and substituted phenyl.

"Substituted phenyl" means a phenyl group in which one or more of the hydrogens has been replaced by the same or different substituents including halo, lower alkyl, halo-lower alkyl, nitro, amino, acylamino, hydroxy, lower alkoxy, aryl lower alkoxy, acyloxy, cyano, halo-lower alkoxy or lower alkyl sulfonyl.

"Aralkyl" means an alkyl (preferably a lower alkyl) in which one or more hydrogens is substituted by an aryl moiety (preferably phenyl or substituted phenyl), e.g., benzyl, phenethyl, etc.

"Heterocyclic group" or "heterocycle" means a 3,5, 6 or 7 membered ring having 1 to 3 hetero atoms which may be nitrogen, oxygen or sulfur, including pyridyl, pyrimidyl, pyrazolyl, imidazolyl, furyl, thienyl, oxazolyl, thiazolyl, piperidyl, morpholinyl, oxazolidinyl, thiazolidinyl, pyrazolidinyl, imidazolidinyl, piperazinyl, thiamorpholinyl, trimethylenetriaminyl and ethyleneiminyl.

"Substituted heterocycle" means a heterocycle in which one or more of the hydrogens on the ring carbons have been replaced by substituents as given above with respect to substituted phenyl.

The terms "halo" and "halogen" include all four halogens; namely, fluorine, chlorine, bromine and iodine. The halo alkyls, halophenyl and halo-substituted pyridyl include groups having more than one halo substituent which may be the same or different such as trifluoromethyl, 1-chloro-2-bromo-ethyl, chlorophenyl, 4-chloropyridyl, etc.

"Acyloxy" means an organic acid radical of a lower alkanoic acid such as acetoxy, propionoxy, and the like.

"Lower alkanoyl" means the acyl radical of a lower alkanoic acid such as acetyl, propionyl, butyryl, valeryl, stearoyl, and the like.

"Alkoxy" is intended to include hydroxy alkyl groups. Preferred lower alkyl groups include methoxy, ethoxy, n-propoxy, i-propoxy, and the like.

"$R_5$ and $R_6$ together with the nitrogen to which they are attached form a 3 to 7 atom ring" means a heterocycle selected from the group including oxazolidinyl, thiazolidinyl, pyrazolidinyl, imidazolidinyl, piperidyl, piperazinyl, thiamorpholinyl, trimethylenetriaminyl, ethyleneiminyl and morpholinyl; where the heterocycle may be mono-, di-, tri- or tetra-substituted by hydrogen, lower alkyl, lower alkenyl, lower alkynyl, aryl, aralkyl, halo, nitro, cyano, sulfonyl, hydroxyl, carboxyl, lower alkanoyl, lower alkoxy, aryl lower alkoxy, halo lower alkoxy, amido, amino, lower alkylamino, aralkylamino, lower alkoxyamino, and aralkylamino.

The preferred "aryl" group is phenyl.

The preferred "aralkyl" groups are benzyl and phenethyl.

The preferred "halo lower alkyl" group is trifluoromethyl.

The preferred "halo lower alkoxy" group is trifluoromethoxy.

It is well known in the pharmacological arts that nontoxic acid addition salts of pharmacologically active amine compounds do not differ in activities from their free base. The salts merely provide a convenient solubility factor.

The amidinoureas of this invention may be readily converted to their nontoxic acid addition salts by customary methods in the art. The nontoxic salts of this invention are formed from the amidinourea base and on acid which is pharmacologically acceptable in the intended dosages. Such salts would include those prepared from inorganic acids, organic acids, higher fatty acids, high molecular weight acids, etc. Exemplary acids are hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, etc.

Representative examples of the compounds of this invention are listed in Tables I and I-A.

TABLE I 1-(2-pyridyl)-3-methylamidinourea
1-(2-pyridyl)-3-ethylamidinourea
1-(2-pyridyl)-3-propylamidinourea
1-(2-pyridyl)-3-i-propylamidinourea
1-(2-pyridyl)-3-butylamidinourea
1-(2-pyridyl)-3-i-butylamidinourea
1-(2-pyridyl)-3-pentylamidinourea
1-(2-pyridyl)-3-propargylamidinourea
1-(2-pyridyl)-3-allylamidinourea
1-(2-pyridyl)-3-methoxyethylamidinourea
1-(2-pyridyl)-3-benzyloxyethylamidinourea
1-(2-pyridyl)-3-phenethoxyethylamidinourea
1-(2-pyridyl)-3-(N,N-dimethylamidino)urea
1-(2-pyridyl)-3-(N,N-diethylamidino)urea
1-(2-pyridyl)-3-(N,N-tetramethyleneamidino)urea
1-(2-pyridyl)-3-(N,N-pentamethyleneamidino)urea
1-(2-pyridyl)-3-(N,N-hexamethyleneamidino)urea
1-(2-[3-methylpyridyl])-3-methylamidinourea 1-(2-[3-methylpyridyl])-3-ethylamidinourea
1-(2-[3-methylpyridyl])-3-propylamidinourea
1-(2-[3-methylpryidyl])-3-i-propylamidinourea
1-(2-[3-methylpyridyl])-3-i-butylamidinourea
1-(2-[3-methylpyridyl])-3-pentylamidinourea
1-(2-[3-methylpyridyl])-3-allylamidinourea
1-(2-[3-methylpyridyl])-3-propargylamidinourea
1-(2-[3-methylpyridyl])-3-cyclopropylamidinourea
1-(2-[3-methylpryidyl])-3-methoxyethylamidinourea
1-(2-[3-methylpyridyl])-3-benzyloxyethylamidinourea
1-(2-[3-methylpyridyl])-3-phenethoxyethylamidinourea
1-(2-[3-methylpyridyl])-3-benzylamidinourea
1-(2-[3-methylpyridyl])-3-(N,N-dimethylamidino)urea
1-(2-[3-methylpyridyl])-3-(N,N-diethylamidino)urea
1-(2-[3-methylpyridyl])-3-(N,N-tetramethyleneamidino)urea
1-(2-[3-methylpyridyl])-3-(N,N-pentamethyleneamidino)urea
1-(2-[3-chloropyridyl])-3-methylamidinourea
1-(2-[3-chloropyridyl])-3-ethylamidinourea
1-(2-[3-chloropyridyl])-3-propylamidinourea
1-(2-[3-chloropyridyl])-3-i-propylamidinourea
1-(2-[3-chloropyridyl])-3-butylamidinourea
1-(2-[3-chloropyridyl])-3-i-butylamidinourea
1-(2-[3-chloropyridyl])-3-t-butylamidinourea
1-(2-[3-chloropyridyl])-3-pentylamidinourea
1-(2-[3-chloropyridyl])-3-allylamidinourea
1-(2-[3-chloropyridyl])-3-propargylamidinourea
1-(2-[3-chloropyridyl])-3-cyclopropylamidinourea
1-(2-[3-chloropyridyl])-3-cyclobutylamidinourea
1-(2-[3-chloropyridyl])-3-([3-cyclopentenyl]amidino)urea
1-(2-[3-chloropyridyl])-3-cyclopropylmethylamidinourea
1-(2-[3-chloropyridyl])-3-methoxyethylamidinourea
1-(2-[3-chloropyridyl])-3-benzyloxyethylamidinourea
1-(2-[3-chloropyridyl])-3-phenethoxyethylamidinourea
1-(2-[3-chloropyridyl])-3-benzylamidinourea
1-(2-[3-chloropyridyl])-3-(N,N-dimethylamidino)urea
1-(2-[3-chloropyridyl])-3-(N,N-diethylamidino)urea
1-(2-[3-chloropyridyl])-3-(N,N-tetramethyleneamidino)urea
1-(2-pyridyl)-3-(N,N[3-methyl-3-azapentamethylene]amidino)urea
1-(2-pryidyl)-3-(N,N[3-oxapentamethylene]amidino)urea
1-(3-pyridyl)-3-methylamidinourea
1-(3-pyridyl)-3-ethylamidinourea
1-(3-pyridyl)-3-propylamidinourea
1-(3-pyridyl)-3-i-propylamidinourea
1-(3-pyridyl)-3-butylamidinourea
1-(3-pyridyl)-3-i-butylamidinourea
1-(3-pyridyl)-3-t-butylamidinourea
1-(3-pyridyl)-3-pentylamidinourea
1-(3-pyridyl)-3-allylamidinourea
1-(3-pyridyl)-3-propargylamidinourea
1-(3-pyridyl)-3-cyclobutylamidinourea
1-(3-pyridyl)-3-cyclohexylamidinourea
1-(3-pyridyl)-3-benzylamidinourea
1-(3-pyridyl)-3-methoxyethylamidinourea
1-(3-pyridyl)-3-benzyloxyethylamidinourea
1-(3-pyridyl)-3-methoxyethylamidinourea
1-(3-pyridyl)-3-benzyloxyethylamidinourea
1-(3-pyridyl)-3-phenethoxyethylamidinourea
1-(3-pyridyl)-3-(N,N-diethylamidino)urea
1-(3-pyridyl)-3-(N,N-dimethylamidino)urea
1-(3-pyridyl)-3-(N,N-pentamethyleneamidino)urea
1-(4-pyridyl)-3-methylamidinourea
1-(4-pyridyl)-3-ethylamidinourea
1-(4-pyridyl)-3-propylamidinourea
1-(4-pyridyl)-3-i-propylamidinourea
1-(4-pyridyl)-3-butylamidinourea
1-(4-pyridyl)-3-t-butylamidinourea
1-(4-pyridyl)-3-pentylamidinourea
1-(4-pyridyl)-3-hexylamidinourea
1-(4-pyridyl)-3-propargylamidinourea
1-(4-pyridyl)-3-allylamidinourea
1-(4-pyridyl)-3-methoxyethylamidinourea
1-(4-pyridyl)-3-benzyloxyethylamidinourea
1-(4-pyridyl)-3-phenethoxyethylamidinourea
1-(4-pyridyl)-3-(N,N-dimethylamidino)urea
1-(4-pyridyl)-3-(N,N-diethylamidino)urea
1-(4-pyridyl)-3-(N-methyl-N-ethylamidino)urea
1-(4-pyridyl)-3-(N,N-tetramethyleneamidino)urea
1-(4-pyridyl)-3-(N,N-pentamethyleneamidino)urea
1-(4-pyridyl)-3-(N,N-hexamethyleneamidino)urea
1-(4-[2-ethylpyridyl])-3-methylamidinourea
1-(4-[2-ethylpyridyl])-3-ethylamidinourea
1-(4-[2-ethylpyridyl])-3-propylamidinourea
1-(4-[2-ethylpyridyl])-3-butylamidinourea
1-(4-[2-ethylpyridyl])-3-i-butylamidinourea
1-(4-[2-ethylpyridyl])-3-pentylamidinourea
1-(4-[2-ethylpyridyl])-3-allylamidinourea
1-(4-[2-ethylpyridyl])-3-propargylamidinourea
1-(4-[2-ethylpyridyl])-3-methoxyethylamidinourea
1-(4-[2-ethylpyridyl])-3-benzyloxyethylamidinourea
1-(4-[2-ethylpyridyl])-3-(N,N-dimethylamidino)urea
1-(4-[2-ethylpyridyl])-3-(N,N-diethylamidino)urea
1-(4-[2-ethylpyridyl])-3-(N,N-tetramethyleneamidino)urea
1-(3-[2,4-dimethylthiophenyl])-3-amidinourea
1-(3[2-chloro-4-methylthiophenyl])-3-methylamidinourea
1-(4-[2,6-dichloropyridyl])-3-methylamidinourea
1-(4-[2,6-dimethylpyridyl])-3-methylamidinourea
1-(4-[2-methyl-6-chloropyridyl])-3-methylamidinourea
1-(2-thiophenyl)-3-methylamidinourea
1-(3-thiophenyl)-3-methylamidinourea
1-(2-[3-methylthiophenyl])-3-methylamidinourea
1-(2-[3-chlorothiophenyl])-3-methylamidinourea
1-(2-pyridyl-N-oxide)-3-(N,N-dimethylamidino)urea
1-(2-[3-cyanopyridyl])-3-methylamidino urea
1-(2-[3-carbomethoxypyridyl])-3-methylamidino urea
1-(2-[3-carboethoxypyridyl])-3-methylamidino urea
1-(2-[6-chloropyridyl])-3-methylamidino urea
1-(2-[6-methylpyridyl])-3-methylamidino urea
1-(2-[3-ethylpyridyl])-3-methylamidino urea
1-(3-[2-methylpyridyl)-3-methylamidino urea
1-(3-[2-ethylpyridyl])-3-methylamidino urea
1-(3-[2,-dimethylpyridyl])-3-methylamidino urea
1-(2-[3-cyanothiophenyl])-3-methylamidino urea
1-(2-[3-carbomethoxythiophenyl])-3-methylamidino urea
1-(2-[3-carboethoxythiophenyl])-3-methylamidino urea
1-(3-[2-methoxypyridyl])-3-methylamidino urea
1-(3-[2-ethoxypyridyl])-3-methylamidino urea
1-(3-[2-chloropyridyl])-3-methylamidino urea
1-(2-furyl)-3-amidinourea
1-(3-furyl)-3-amidinourea
1-(2-[3-methylfuryl])-3-amidinourea
1-(2-furyl)-3-ethylamidino urea
1-(2-furyl)-3-propylamidino urea
1-(2-furyl-3-i-propylamidino urea
1-(2-furyl)-3-butylamidino urea
1-(2-furyl)-3-i-butylamidino urea
1-(2-furyl)-3-sec-butylamidino urea 1-(2-furyl)-3-t-butylamidino urea
1-(2-furyl)-3-pentylamidino urea
1-(2-furyl)-3-hexylamidino urea
1-(2-furyl)-3-heptylamidino urea
1-(2-furyl)-3-cyclopropylamidino urea
1-(2-furyl)-3-cyclobutylamidino urea
1-(2-pyridyl-N-oxide)-3-methylamidinourea
1-(3-pyridyl-N-oxide)-3-methylamidinourea
1-(4-pyridyl-N-oxide)-3-methylamidinourea
1-(2-furyl)-3-methylamidinourea
1-(3-furyl)-3-methylamidinourea
1-(2-tetrahydrofuryl)-3-methylamidinourea
1-(3-tetrahydrofuryl)-3-methylamidinourea
1-(1-imidazolyl)-3-methylamidinourea
1-(2-imidazolyl)-3-methylamidinourea
1-(4-imidazolyl)-3-methylamidinourea
1-(2-oxazolyl)-3-methylamidinourea
1-(4-oxazolyl)-3-methylamidinourea
1-(5-oxazolyl)-3-methylamidinourea
1-(1-pyrazolyl)-3-methylamidinourea
1-(1-[3-pyrrolidyl])-3-methylamidinourea
1-(2-pyrrolyl)-3-methylamidinourea
1-(1-morpholinyl)-3-methylamidinourea
1-(2-morpholinyl)-3-methylamidinourea
1-(2-pyrimidinyl)-3-methylamidinourea
1-(4-pyrimidinyl)-3-methylamidinourea
1-(2-quinolinyl)-3-methylamidinourea
1-(4-quinolinyl)-3-methylamidinourea
1-(1-isoquinolinyl)-3-methylamidinourea
1-(2-furyl)-3-cyclopentylamidino urea
1-(2-furyl)-3-cyclohexylamidino urea
1-(2-furyl)-3-phenylamidino urea
1-(2-furyl)-3-benzylamidino urea
1-(2-furyl)-3-phenethylamidino urea
1-(2-furyl)-3-(N-methyl-N-benzylamidino)urea
1-(2-furyl)-3-(N,N-dibenzylamidino)urea
1-(2-tetrahydrofuryl)-3-amidinourea
1-(2-[3-methyltetrahydrofuryl])-3-amidinourea
1-(3-tetrahydrofuryl)-3-amidinourea
1-(3-[2-methyltetrahydrofuryl])-3-amidinourea
1-(1-imidazolyl)-3-amidinourea
1-(1-[2-methylimidazolyl])-3-amidinourea
1-(3-[2,4-dichlorothiophenyl])-1-methyl-3-amidinourea

TABLE I-A

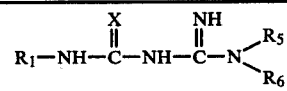

X may be oxygen or sulfur

| $R_1$ | $R_5$ | $R_6$ |
|---|---|---|
| 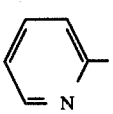 | H | H |
| 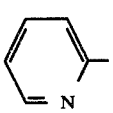 | H | —CH$_3$ |

TABLE I-A-continued

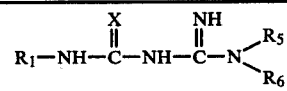

X may be oxygen or sulfur

| $R_1$ | $R_5$ | $R_6$ |
|---|---|---|
| 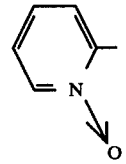 | H | —C$_2$H$_5$ |
| 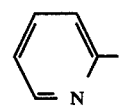 | —CH$_3$ | —CH$_3$ |
| 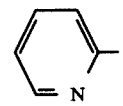 | H | —OCH$_3$ |
| 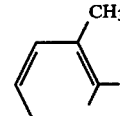 | H | —CH$_3$ |
| 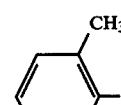 | —CH$_3$ | —CH$_3$ |
| 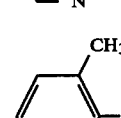 | —C$_2$H$_5$ | —C$_2$H$_5$ |
| 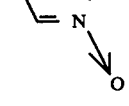 | H | H |
| 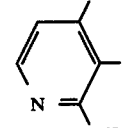 | H | —CH$_3$ |
| 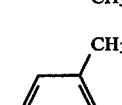 | H | —C$_2$H$_5$ |

TABLE I-A-continued $$R_1-NH-\overset{X}{\underset{\|}{C}}-NH-\overset{NH}{\underset{\|}{C}}-N\overset{R_5}{\underset{R_6}{\diagdown}}$$

X may be oxygen or sulfur

| $R_1$ | $R_5$ | $R_6$ |
|---|---|---|
| 3,5-dimethylpyridin-4-yl | H | —OCH₃ |
| 3,5-dimethylpyridin-4-yl | —CH₃ | —CH₃ |
| 3,5-dimethylpyridin-4-yl | —CH₃ | —C₂H₅ |
| 3-ethylpyridin-2-yl N-oxide | H | H |
| 3-ethylpyridin-2-yl | H | —CH₃ |
| 3-ethylpyridin-2-yl | H | —C₂H₅ |
| pyrimidin-2-yl | H | H |
| pyrimidin-2-yl | H | —CH₃ |
| pyrimidin-2-yl | —CH₃ | —CH₃ |
| pyrimidin-2-yl | —H | —CH₃ |
| pyrimidin-2-yl | —H | —C₂H₅ |
| pyrimidin-2-yl | —CH₃ | —CH₃ |
| 4,6-dimethylpyrimidin-5-yl | H | H |
| 4,6-dimethylpyrimidin-5-yl | H | —CH₃ |
| 4,6-dimethylpyrimidin-5-yl | —CH₃ | —CH₃ |
| 4,6-dimethylpyrimidin-5-yl | H | —C₂H₅ |
| pyridin-4-yl | H | H |
| pyridin-4-yl | H | —CH₃ |
| imidazol-2-yl (1H) | H | H |

TABLE I-A-continued

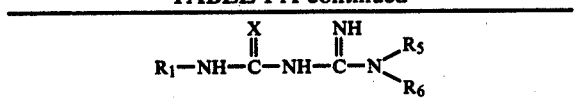

X may be oxygen or sulfur

| R₁ | R₅ | R₆ |
|---|---|---|
| 2-imidazolyl (NH) | H | —CH₃ |
| 2-imidazolyl (NH) | H | —C₂H₅ |
| 4(5)-imidazolyl (NH) | H | H |
| 4(5)-imidazolyl (NH) | H | —CH₃ |
| 2-furyl | H | —CH₃ |
| 2-furyl | H | H |
| 3-furyl | H | —CH₃ |
| 3-furyl | H | —C₂H₅ |
| 2-thienyl | H | —CH₃ |
| 2-thienyl | —CH₃ | —CH₃ |
| 1-methyl-2-pyrrolyl | —H | —CH₃ |
| 1-methyl-2-pyrrolyl | —H | —C₂H₅ |
| 5-isoxazolyl | —H | —CH₃ |
| 3,5-dichloro-4-pyridyl | H | —CH₃ |
| 3,5-dichloro-4-pyridyl | H | —C₂H₅ |
| 3-chloro-2-thienyl | H | —CH₃ |
| 3-chloro-2-thienyl | H | —C₂H₅ |
| 3,5-dimethyl-2-thienyl (4-CH₃) | H | —CH₃ |
| 3,5-dimethyl-2-thienyl (4-CH₃) | H | —C₂H₅ |
| 5-chloro-3-methyl-2-thienyl | H | —CH₃ |
| 5-chloro-3-methyl-2-thienyl | H | —C₂H₅ |

TABLE I-A-continued $$R_1-NH-\overset{X}{\underset{\|}{C}}-NH-\overset{NH}{\underset{\|}{C}}-N\overset{R_5}{\underset{R_6}{}}$$

X may be oxygen or sulfur

| $R_1$ | $R_5$ | $R_6$ |
|---|---|---|
| 4-methyl-5-chloro-thiophen-2-yl | H | $-CH_3$ |
| isothiazol-5-yl | H | $-CH_3$ |
| isothiazol-5-yl | H | $-C_2H_5$ |
| isoxazol-5-yl | H | $-CH_3$ |
| 1,2,3,4-tetrahydroquinolin-2-yl (NH) | H | $-C_2H_5$ |
| quinolin-2-yl | H | $-CH_3$ |
| 1,2,3,4-tetrahydroquinolin-2-yl (N-) | H | $-C_2H_5$ |
| isoquinolin-3-ylmethyl | H | $-CH_3$ |
| isoquinolin-3-yl | H | $-C_2H_5$ |
| indol-2-yl (NH) | H | $-CH_3$ |
| indol-2-yl (N-) | H | $-C_2H_5$ |

The compounds of this invention may be prepared by the following general synthesis.

Condensation of a N-heterocyclic carbamate, for example a phenyl-N-heterocyclic carbamate, with an appropriately substituted guanidine results in a 1-heterocyclic-3-substituted amidinourea. The reaction is carried out in a polar media using solvents such as alcohol, tetrahydrofuran, etc. It is convenient to carry out the reaction by preparing the guanidine in situ by hydrolyzing a guanidine carbonate with base. Condensation of the carbamate takes place when the guanidine forms and the amidinourea compounds result.

When $R_2$ substitution is desired, the starting material can be a N-heterocyclic N-substituted carbamate, obtained from the corresponding N-alkyl heterocyclic amine, which is then reacted with the appropriate substituted guanidine to prepare the amidinourea. (Scheme I)

Scheme I

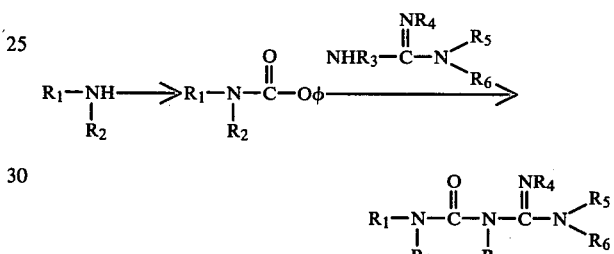

One method to obtain an amidinothiourea is where the starting material is a triethylamine salt of a heterocyclic dithiocarbamic acid which can be obtained from the heterocyclic amine. Reaction with $FeCl_3$ eliminates $H_2S$ to form the isothiocyanate. Subsequent reaction with an appropriate substituted guanidine forms the heterocyclic amidinothiourea. (Scheme II)

Scheme II

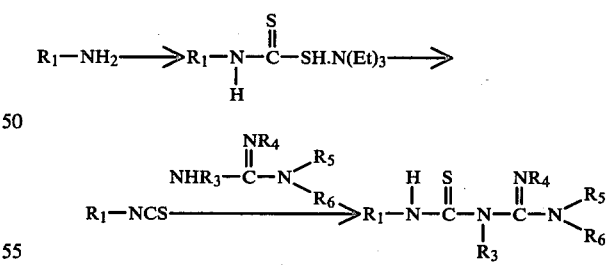

The starting heterocyclic amines are known or may be prepared by known techniques.

Reactions may also be carried out at other stages of synthesis depending on the substituents present and the substituents desired. Various combinations of the foregoing reactions can be determined by one skilled in the art in order that the desired product results. Thus, a pyridylamidinourea may be halogenated or nitrated, etc.

The following are detailed examples which show the preparation of the compounds of this invention.

EXAMPLE I

The preparation of
1-methyl-3-[(2-pyridyl-1-oxide)carbamoyl]guanidine

Step 1

2-Oxo-2H-[1,2,4[oxadiazolo]2,3-a]pyridine

2-Ethoxy carbonyl amino pyridine-1-oxide (41.90 g) is heated to 140°–150° C. for one hour and then 150°–160° C. for an additional hour with removal of ethyl alcohol. The resulting solid is cooled, recrystallized from absolute ethanol, and dried to afford 9.87 grams of tan crystals, M.P. 203°–205° C.

Step 2

1-methyl-3-[(2-pyridyl-1-oxide)carbamoyl]guanidine

Finely powdered methyl quanidine sulfate (7.33 g) is added to a stirred solution of NaOCH$_3$ (3.24 g) in 20 ml absolute ethanol. The mixture is stirred at room temperature for three hours and filtered through a celite pad. The filtrate is evaporated in vacuo and the residual oil is triturated with dry toluene to yield a white solid. The toluene is evaporated in vacuo. 2-Oxo-2H-(1,2,4[oxadiazolo]2,3-a)pyridine (8.17 g) in 150 ml of dry toluene is added to the white solid and the reaction mixture heated to reflux for 30 minutes. A brown solid forms. The reaction mixture is stirred under reflux for an additional 30 minutes. A brown crystalline solid is collected, washed with toluene and dried. The solid is recrystallized from absolute ethanol to give a 24% yield of the desired amidinourea as a white solid, M.P. 177°–179° (dec).

EXAMPLE II

Preparation of
1-(2-chloro-4-bromo-6-methylphenyl)-3-[(2-pyridyl-1-oxide)carbamoyl]-guanidine A mixture of 1-(2-chloro-4-bromo-6-methylphenyl)-guanidine (13.13 g), and 2-Oxo-2H-[1,2,4]oxadiazolo[2,3-a]pyridine (6.81 g) in 150 ml of dry toluene is heated slowly to boiling for one hour and stirred under gentle reflux overnight. The reaction mixture is cooled to room temperature and the solid collected, washed with toluene and dried to afford 16.34 grams of a gray powder. The gray powder is extracted with 1.5 l of boiling acetonitrile, filtered through celite, and concentrated to approximately 500 ml and cooled. A crystalline solid is formed which is washed with acetonitrile, and dried to afford 8.58 grams of the desired N-oxide as gray crystals, M.P. 175°–176° C. (dec).

EXAMPLE III 1-(2-pyridyl)-3-methylamidinourea

A 50% aqueous sodium hydroxide solution (6.54 g) is added to a stirred suspension of methyl guanidine sulfate (9.77 g) and 500 ml of THF. The suspension is stirred for ½ hour and anhydrous Na$_2$SO$_4$ (20 g) is added. The reaction mixture is stirred ½ hour and phenyl-N-(2-pyridyl)carbamate (17.12 g) is added. The reaction mixture is stirred for four hours and the reaction mixture filtered. The residue is taken up with 500 ml of boiling methanol and filtered. The filtrate is concentrated in vacuo, taken up in chloroform and washed with water and brine. The aqueous washes were back extracted and the organic extracts combined, dried, filtered and concentrated in vacuo to yield a yellow oil. [A white solid is insoluble in both water and organic layers. This solid is filtered, washed and dried to give a white solid, M.P. 183.5°–185° C. The residue filtrate from above is concentrated to 300 ml and a precipitate is formed. Precipitate has a melting point of 186°–188° C.] The yellow oil is taken up in 100 ml of chloroform, washed, dried, filtered and concentrated in vacuo to yield a white solid, M.P. 182°–183° C. The white solids are combined to give 10.7 grams of crude amidinourea. The hydrochloric acid salt is formed by partially dissolving the white solids in boiling methanol and acidifying with methanolic HCl. The methanolic solution is concentrated in vacuo to yield a white solid which is dissolved in methanol and filtered through charcoal and celite. The filtrate is concentrated and the resultant solid recrystallized from methanol/acetonitrile to yield the desired hydrochloric acid salt, M.P. 164.5°–165° C.

EXAMPLE IV

The preparation of
1-(2,5-dimethylpyrrole)-3-methylamidinourea 3.2 grams of a 50% aqueous sodium hydroxide solution are added to a suspension of N-methylguanidine sulfate (4.89 g) in 75 ml THF. The suspension is stirred for 45 minutes and anhydrous sodium sulfate added. The suspension is stirred for an additional hour at room temperature and a solution of N-2,5-dimethylpyrrolyl-O-phenylcarbamate (4.61 g) in 50% ml THF is added dropwise. The reaction mixture is stirred at RT for one week, evaporated in vacuo and the residue partitioned between water and chloroform. The aqueous layer is washed with chloroform. The organic layer is combined, back extracted and dried. The chloroform is evaporated in vacuo and the product residue titriated in ether to give 0.68 gram of a yellow solid, M.P. 180°–182° C.

EXAMPLE V 1-(2-pyridyl)-3-methoxyamidinourea hydrochloride 2.6 grams of a 50% aqueous sodium hydroxide solution are added to a suspension of methoxy guanidine hydrochloride (4.1 g) in 50 ml of THF. The reaction mixture is stirred for one hour, anhydrous sodium sulfate (5.0 g) added and the mixture stirred for an additional hour. The mixture is filtered and the solid material washed well with THF. The THF is removed to give 3.0 grams of a semi-crystalline solid. This material is dissolved in 100 ml of THF to which is added phenyl N-(2-pyridyl)carbamate (6.4 g) and the mixture stirred at RT over the weekend. The THF is removed in vacuo and the residue dissolved in chloroform and passed through a column of 18 grams of silica gel. The column is washed with ethyl acetate and the ethyl acetate fraction dissolved in methanol and acidified with methanolic HCl. The methanol is removed in vacuo to give a foam which is crystallized from acetonitrile to give 0.4 gram of the desired hydrochloride salt as a pink solid, M.P. 152°–153° C.

EXAMPLE VI

The preparation of 1-[2-(5-chloropyridyl)]-3-methylamidinothiourea hydrochloride

Step 1

5-chloro-2-isothiocyanate pyridine

A solution of $FeCl_3 \cdot 6H_2O$ (59.5 g) in 240 ml of $H_2O$ is rapidly added to a stirred suspension of 5-chloro-2-pyridyl dithiocarbamic acid triethylamine salt (61.4 g) in 250 ml of methylene chloride containing 20.2 grams of triethylamine. The reaction mixture is stirred for 5 minutes and then poured through a celite pad. The celite pad is washed with methylene chloride. The layers of the filtrate are separated and the aqueous layer extracted with methylene chloride. The combined organic extracts are dried, concentrated in vacuo to give an orange solid. The residue is extracted with dry refluxing ether and the combined extracts concentrated in vacuo to give a yellow orange solid. This material is taken up in hexane and filtered. The filtrate is concentrated in vacuo to give 7.8 grams of an orange solid which is sublimed (70° C./vacuum pump) to give 4.3 grams of the thioisocyanate, M.P. 44°–44.5° C.

Step 2

1-[2-(5-chloropyridyl)]-3-methylamidinothiourea hydrochloride 2.1 grams of a 50% aqueous sodium hydroxide solution are added to a stirred suspension of methyl guanidine sulfate (3.2 g) in 100 ml of THF and the mixture stirred for one hour. 6.0 grams of anhydrous sodium sulfate are added and the mixture stirred an additional hour. A solution of 5-chloro-2-isothiocyanatopyridine (4.2 g) in 80 ml THF is added to the reaction mixture over a period of one and one-half hours and the mixture stirred for an additional hour. The reaction mixture is filtered and concentrated in vacuo to give an orange red foam which is partitioned between methylene chloride and water. Saturated sodium chloride is added to break up the emulsion and the layers are separated. The aqueous layers are extracted with methylene chloride and the combined extracts are dried and concentrated under reduced pressure. The residual oil solidifies on standing. The solid is crystallized from ethyl acetate to give 3.6 grams of a light yellow solid. The solid is taken up in methanol and acidified with methanolic HCl. The solution was filtered through a celite pad and the filtrate concentrated in vacuo to give a yellow solid which is crystallized from methanol/acetonitrile to give 3.9 grams of a light yellow powder. This material is recrystallized from 95% ethanol to give 2.9 grams of the desired hydrochloride salt, M.P. 193°–194° C. (dec.)

EXAMPLE VII

The preparation of 1-amidino-3-(2-chloro-4-methyl-3-thienyl)urea hydrochloride

Step 1

2-Chloro-3-isocyanato-4-methylthiophene

A solution of 2-chloro-4-methyl-3-thiophene carboxylic acid (44.16 g) and thionyl chloride (36 ml, 59.5 g) in toluene (1 liter) is stirred under reflux for 20 hours. The reaction mixture is evaporated under reduced pressure and the resultant yellow-brown oil dissolved in 280 ml of acetone and cooled in a methanol-ice bath. A solution of sodium azide (69.07 g) in $H_2O$ (265 ml) is added dropwise to the vigorously stirred reaction mixture while maintaining the reaction temperature below 0° C. After the addition is complete, the mixture is stirred for 1 hour, and concentrated under reduced pressure at RT. The concentrate is extracted with carbon tetrachloride, and the extracts washed (sat'd aq. NaCl), dried ($MgSO_4$), filtered and concentrated under reduced pressure to a volume of about 500 ml. The concentrated extract is heated slowly to boiling while controlling temperature by cooling. Heating is accompanied by rapid gas evolution. The concentrated extract is refluxed overnight. The concentrated extract is evaporated under reduced pressure and the residue distilled, affording 33.57 g of the thiophenyl isocyanate as a water-white liquid, b.p. 42° C. (0.20 mm).

Step 2

1-Amidino-3-(2-chloro-4-methyl-3-thienyl)urea hydrochloride

A mixture of guanidine hydrochloride (14.33 g), and 50% aqueous NaOH (10.00 g) in THF (250 ml) is stirred at room temperature overnight. THF (250 ml), and anhydrous $Na_2SO_4$ (7.5 g) are added to the mixture and stirring continued for 1 hour. A solution of 2-chloro-3-isocyanato-4-methylthiophene (8.68 g) in THF (500 ml) is added dropwise to the stirred mixture. After the addition is complete, stirring is continued for 30 minutes. The solvent is decanted, leaving a THF insoluble material. The solvent is evaporated under reduced pressure. The evaporated residue is suspended in 500 ml of 2% aqueous HCl and added to the THF insoluble material. This mixture is stirred vigorously with 250 ml of $Et_2O$ for 30 minutes. Insoluble material is separated by decantation. The aqueous layer is separated, washed with $Et_2O$ and alkalinized with $NaHCO_3$, forming a precipitate. The precipitate is washed with $H_2O$ and air dried to afford 8.85 g of a tan crystalline solid. The tan solid is dissolved in 5% aqueous HCl (175 ml), filtered through Celite, and the filtrate cooled rapidly to room temperature. After standing overnight in the cold, the precipitate is collected, washed with a portion of the mother liquor, dried in vacuo, and stirred in 100 ml of $CH_2Cl_2$, and air dried in vacuo (50° C.) overnight to yield 7.20 g of the amidinourea hydrochloride as a tan powder, m.p. 173°–174.5° C. w/dec.

This invention also relates to a method for lowering blood pressure in mammalian species by administering to a patient an effective blood pressure lowering amount of a compound according to Formula I, and preferably, a compound according to Formula VII:

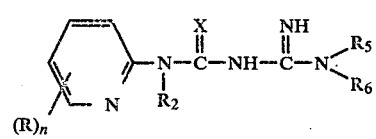

where:
X is O or S;
n is zero to four;
(R) is a ring substituent as defined above including pyridyl N-oxide
$R_2$ is hydrogen or alkyl;
$R_5$ and $R_6$ are hydrogen, alkoxy, alkenyl, alkyl, or aryl;

and the pharmaceutically acceptable salts thereof.

Various tests can be carried out in animal models to show the ability of the compounds of this invention to exhibit reactions that can be correlated with pharmacological activity in humans. The following test protocol can be used to determine the blood pressure effect of compounds according to this invention.

Determination of Antihypertensive Activity

A description of the test protocol used in the determination of the antihypertensive activity of the compounds of this invention follows:

(a) Male TAC spontaneously hypertensive rats (SHR's), eleven weeks old, weighing 200–220 grams, are chosen for testing. The average systolic blood pressure (as measured below) should be 165 mmHg or above. Any rat not initially meeting this criterion is not utilized.

(b) A Beckman dynograph is balanced and calibrated using a Beckman indirect blood pressure coupler. A mercury monometer is placed on one arm of the glass "T" tube. The known pressure head in the tail cuff is synchronized with the recorder output so that 1 mm pen deflection=5 mmHg. Any correction is made using the chart calibration screw on the pressure coupler. The pulse amplitude is controlled by the pre-amplifier using a 20 v/cm setting.

The rats are prewarmed in groups of five for twenty minutes to dilate the tail artery from which the arterial pulse is recorded. After prewarming, each rat is placed in an individual restraining cage with continued warming. When the enclosure temperature has been maintained at 35° C. for 5 minutes, recordings are started. The tail cuff is placed on the rat's tail and the rubber bulb of the pneumatic tail cuff transducer is taped securely to the dorsal surface of the tail. When the rat's pulse reaches maximum amplitude and is unwavering, the cuff is inflated and the air slowly released. A reading of systolic blood pressure is read at the point of the chart when the first deflection appears on the chart recording while the air in the cuff is being released. The exact point of the systolic blood pressure reading is where the first deflection forms a 90° angle to the falling cuff pressure base line. After obtaining nine or ten consistent readings, the average of the middle five readings is calculated.

(c) Three groups of twenty rats receive the test compound at doses of 0.125 mg/kg, 0.5 mg/kg, and 2 mg/kg b.i.d. A fourth group of twenty control rats receives distilled water. Statistical comparisons of systolic pressure (four hours after the first dose and sixteen hours after the second dose) are made on a daily basis using the Student t test for dependent variables (see, E. Lord, Biometrika, 34, 56 (1947)), with the predose observations serving as baseline values for each rat.

The test results on compounds according to Formulae I and VII show that these compounds possess significant blood pressure lowering activity and are useful in lowering blood pressure in humans and animals. In particular, compounds of Formula VII are useful for relieving hypertensive disorders by administering to a patient suffering from hypertension a therapeutically effective amount between about 0.5 mg to about 500 mg per dosage unit of at least one of said compounds.

This invention also relates to a method of treating gastrointestinal disorders by administering to a patient compounds according to Formula I, and preferably compounds according to Formula VIII:

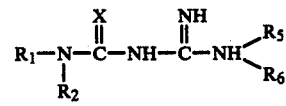

where:
X is oxygen or sulfur;
$R_1$ is pyridyl, 1-pyrrole, substituted 2-pyridyl, substituted 2-pyrrole or substituted 3-thienyl;
$R_2$ is hydrogen or alkyl;
$R_5$ and $R_6$ are each independently hydrogen, alkyl, alkenyl, alkoxy or aryl;

and the pharmaceutically acceptable salts thereof.

Various tests can be carried out in animal models to show the ability of these compounds to exhibit gastrointestinal activity. These tests are well known in the art and are disclosed in U.S. patents discussed above and are hereby incorporated by reference.

One such test is the gastric secretion inhibition test, the test protocol of which is as follows.

The method used has been reported by Shay. Male Sprague-Dawley rats (140–160 g) are fasted 24 hours prior to the test. The rats are allowed water ad libitum only during the fasting period. One hour before pyloric ligation the rats (5/group) are given either atropine sulfate or the vehicle. The compounds are prepared in methylcellulose. Pyloric ligation is performed in the rats under sodium methohexital anesthesia. Four hours after pyloric ligation, the rats are sacrificed by cervical dislocation, the stomachs are removed, and the gastric contents are assayed for volume, titratable acidity, and titratable acid output (TAO). A 1 ml aliquot of the gastric contents are titrated with 0.1 N NaOH to pH 7.0 for titratable acidity. The percent of inhibition is calculated according to the formula $$\frac{\text{Mean control} - \text{mean treated}}{\text{Mean control}} \times 100$$

It has been found that the compounds of this invention, particularly the compounds of Formula VIII possess the ability to markedly decrease gastric volume and gastric acidity and are useful as antisecretory, antidiarrheal and anti-ulcerogenic agents.

The compounds of Formula I are useful for relieving gastrointestinal hyperacidity or ulceration by administering to a patient suffering from said gastrointestinal hyperacidity or ulceration a therapeutically effective amount between about 0.5 mg and about 500 mg per dosage unit of at least one of said compounds.

The compounds of Formula I are also useful for relieving diarrheal conditions by administering to a patient suffering from said diarrheal condition a therapeutically effective amount between about 0.5 mg and about 500 mg per dosage unit of at least one of said compound.

We claim:

1. A compound of the formula

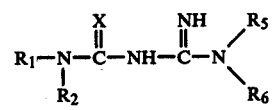

wherein:
X is O or S;

$R_2$ is hydrogen or lower alkyl;

$R_5$ and $R_6$ are hydrogen, lower alkyl, phenyl, substituted phenyl, phenyl loweralkyl, substituted phenyl loweralkyl, cycloloweralkyl, lower alkoxy, or lower alkenyl;

$R_1$ is one of the following pyridyl groups;

[Three pyridyl ring structures with $(R)_n$ substituents]

wherein n is 0 or 1; and (R) is a ring substituent selected from the group consisting of lower alkyl, lower alkoxy, lower alkenyl, lower alkynyl, phenyl, phenyl loweralkyl, loweralkyl phenyl loweralkyl, nitro, sulfonyl, carbamoyl, halo, cyano, carboxyl, amino, lower alkanoyl, amino lower alkyl, lower alkyl amido, hydroxy, halo lower alkyl, lower alkanoyloxy, and lower alkanoylamino;

and wherein substituted phenyl means a phenyl group in which one or more of the hydrogens has been replaced by the same or different substituents including halo, or lower alkyl;

or a non-toxic pharmaceutically acceptable salt thereof.

2. A compound according to the formula $$R_1-\underset{R_2}{N}-\overset{X}{\underset{\|}{C}}-NH-\overset{NH}{\underset{\|}{C}}-N\overset{R_5}{\underset{R_6}{\diagdown}}$$

wherein:

X is O or S;

$R_2$ is hydrogen or lower alkyl;

$R_5$ and $R_6$ are hydrogen, lower alkyl, cycloloweralkyl, lower alkoxy, phenyl, substituted phenyl, phenyl loweralkyl, substituted phenyl loweralkyl, or lower alkenyl;

$R_1$ is one of the following pyridyl N-oxide groups

[Three pyridyl N-oxide ring structures with $(R)_n$ and O substituents]

wherein n is 0 or 1; and (R) is a ring substituent selected from the group consisting of lower alkyl, lower alkoxy, lower alkenyl, lower alkynyl, phenyl, phenyl loweralkyl, loweralkyl phenyl loweralkyl, nitro, sulfonyl, carbamoyl, halo, cyano, carboxyl, amino, lower alkanoyl, amino lower alkyl, lower alkyl amido, hydroxy, halo lower alkyl, lower alkanoyloxy, and lower alkanoylamino;

and wherein substituted phenyl means a phenyl group in which one or more of the hydrogens has been replaced by the same or different substituents including halo or lower alkyl;

or a non-toxic pharmaceutically acceptable salt thereof.

3. A compound according to the formula

[Pyridine ring structure with $R_a, R_b, R_c, R_d$ substituents and side chain: $-\underset{R_2}{N}-\overset{X}{\underset{\|}{C}}-N=C\overset{NH_2}{\underset{N\diagdown R_6}{\diagup R_5}}$]

wherein:

X is oxygen or sulfur;

$R_2$ is hydrogen or lower alkyl;

$R_5$ and $R_6$ are hydrogen, lower alkyl, lower alkoxy, lower alkenyl phenyl, or substituted phenyl;

one of $R_a$, $R_b$, $R_c$, and $R_d$ is other than hydrogen, and is lower alkyl, lower alkoxy, lower alkenyl, lower alkynyl, phenyl, phenyl loweralkyl, loweralkyl phenyl loweralkyl, lower alkanoyl, caramoyl, sulfonyl, halo, carboloweralkoxy, lower alkanoyloxy, phenyl loweralkoxy, substituted phenyl loweralkoxy, hydroxy, cyano, nitro, lower alkanoylamino, carbamoyl, halo lower alkyl amino, lower alkyl amino, amino lower alkyl or hydroxyl;

and wherein substituted phenyl means a phenyl group in which one or more of the hydrogens has been replaced by the same or different substituents including halo or lower alkyl;

or a non-toxic pharmaceutically acceptable salt thereof.

4. A compound according to claim 3 where:
$R_2$ and $R_5$ are hydrogen; and
one of $R_a$, $R_b$, $R_c$, or $R_d$ is halo or lower alkyl;
or a non-toxic acid addition salt thereof.

5. 1-methyl-3-[(2-pyridyl-1-oxide)carbamoyl]guanidine; or a non-toxic acid addition salt thereof.

6. 1-(2-pyridyl)-3-methylamidinourea; or a non-toxic acid addition salt thereof.

7. 1-(2-pyridyl)-3-methoxyamidinourea; or a non-toxic acid addition salt thereof.

8. 1-[2-(5-chloropyridyl)]-3-methylamidinothiourea; or a non-toxic acid addition salt thereof.

9. 1-(2-chloro-4-bromo-6-methylphenyl)-3-[(2-pyridyl-1-oxide) carbamoyl]guanidine; or a non-toxic acid addition salt thereof.

10. A compound of the formula $$R_1-\underset{R_2}{N}-\overset{X}{\underset{\|}{C}}-NH-\overset{NH}{\underset{\|}{C}}-N\overset{R_5}{\underset{R_6}{\diagdown}}$$

wherein:

X is O or S;

$R_2$ is hydrogen or lower alkyl;

$R_5$ and $R_6$ are hydrogen, lower alkyl, cyccloloweralkyl, lower alkoxy or lower alkenyl;

$R_1$ is one of the following pyridyl groups:

[Three pyridyl ring structures with $(R)_n$ substituents]

-continued

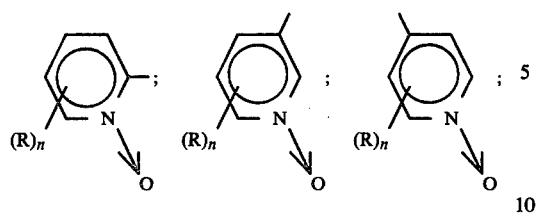

and wherein n is 0 or 1; and (R) is a ring substituent selected from the group consisting of lower alkyl, lower alkoxy, lower alkenyl, lower alkynyl, phenyl, phenyl loweralkyl, loweralkyl phenyl loweralkyl, nitro, sulfonyl, carbamoyl, halo, cyano, carboxyl, amino, lower alkanoyl, amino loweralkyl, lower alkyl amido, hydroxy, halo loweralkyl, lower alkanoyloxy, and lower alkanoylamino; or a non-toxic pharmacetically acceptable salt thereof.

11. A compound according to claim 10 wherein:
X is oxygen;
$R_2$ is hydrogen; and
$R_1$ is one of the following pyridyl groups:

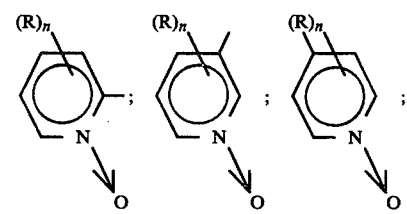

or a non-toxic pharmaceutically acceptable salt thereof.

12. A compound according to claim 10 wherein:
X is sulfur;
$R_2$ is hydrogen; and
$R_1$ is one of the following pyridyl groups:

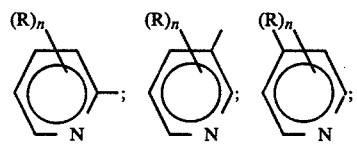

or a non-toxic pharmaceutically acceptable salt thereof.

* * * * *